(12) United States Patent
Popwell et al.

(10) Patent No.: US 11,708,209 B2
(45) Date of Patent: Jul. 25, 2023

(54) TOUCHLESS CONTACT LENS PACKAGES AND METHODS OF HANDLING

(71) Applicant: Johnson & Johnson Vision Care, Inc., Jacksonville, FL (US)

(72) Inventors: Sam Jonathan Popwell, Jacksonville, FL (US); Daniel Graham Ward, Cambridge (GB); Stephen Sams, Cambridge (GB); William Stephen Honey, Cambridge (GB)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 0 days.

(21) Appl. No.: 17/519,973

(22) Filed: Nov. 5, 2021

(65) Prior Publication Data
US 2023/0143203 A1    May 11, 2023

(51) Int. Cl.
*B65D 81/22* (2006.01)
*B65D 85/38* (2006.01)
*B65D 77/20* (2006.01)
*A61F 9/00* (2006.01)

(52) U.S. Cl.
CPC ............ *B65D 81/22* (2013.01); *A61F 9/0061* (2013.01); *B65D 77/2024* (2013.01); *B65D 85/38* (2013.01); *B65D 2585/545* (2013.01)

(58) Field of Classification Search
CPC ........ A45C 11/005; A61F 9/00; A61F 9/0061; B65D 77/20; B65D 77/2024; B65D 81/22; B65D 85/38; B65D 2585/545
USPC ........................................................ 206/5.1
See application file for complete search history.

(56) References Cited

U.S. PATENT DOCUMENTS

| | | | | |
|---|---|---|---|---|
| 3,089,500 A | * | 5/1963 | Stalcup | A45C 11/005 D3/264 |
| 3,524,455 A | * | 8/1970 | Hoogesteger | A45C 11/005 134/143 |
| 4,392,569 A | | 7/1983 | Shoup | |
| 4,415,076 A | * | 11/1983 | Campbell | A45C 11/005 206/5.1 |
| 4,942,959 A | * | 7/1990 | Sauber | A45C 11/005 422/301 |
| 5,099,987 A | * | 3/1992 | Bieri | A45C 11/005 220/663 |
| 5,227,039 A | * | 7/1993 | Pankow | G02C 13/008 204/600 |

(Continued)

FOREIGN PATENT DOCUMENTS

| | | | | |
|---|---|---|---|---|
| FR | 2777360 A1 | * | 10/1999 | ........... A61L 12/086 |
| GB | 2551530 A | | 12/2017 | |
| WO | 9921519 A1 | | 5/1999 | |

OTHER PUBLICATIONS

Extended European Search Report Received for European Patent Application No. 22205781.2, dated Apr. 21, 2023, 8 Pages.

*Primary Examiner* — Bryon P Gehman

(57) ABSTRACT

The present invention relates to improved contact lens packages and methods of use, manufacture, and assembly. A contact lens package houses a contact lens and packaging solution in which the contact lens may be held by surface tension to an intermediate plug, by which the user may insert the contact lens into the wearer's eye. The plug may have an adhesive that temporarily holds the plug to the user's fingertip while the contact lens is inserted into the wearer's eye.

35 Claims, 4 Drawing Sheets

(56) References Cited

U.S. PATENT DOCUMENTS

| | | | |
|---|---|---|---|
| 5,407,062 A * | 4/1995 | Shannon | B29D 11/00125 |
| | | | 134/901 |
| 5,515,964 A * | 5/1996 | Bauman | A45C 11/005 |
| | | | 206/210 |
| 5,695,049 A | 12/1997 | Bauman | |
| 5,732,990 A | 3/1998 | Yavitz et al. | |
| 7,540,376 B2 * | 6/2009 | Mahieu | A45C 11/005 |
| | | | 220/324 |
| 11,071,644 B2 * | 7/2021 | Greenwood | B65D 85/00 |
| 11,136,176 B2 * | 10/2021 | Almond | A45C 11/005 |
| 2012/0267262 A1 | 10/2012 | Wang et al. | |
| 2018/0340622 A1 * | 11/2018 | Godfrey | A45C 11/005 |

* cited by examiner

TOUCHLESS CONTACT LENS PACKAGES AND METHODS OF HANDLING

I. BACKGROUND OF THE INVENTION

In a conventional contact lens package, the contact lens typically sits in a molded plastic base having a cavity (or "bowl") that houses the contact lens in a concave-side-up orientation. As a result, the user experience for transferring a contact lens from the package to an eye generally involves the user "fishing" the contact lens out of the bowl with a finger and then flipping the lens so that it is in the correct orientation on the finger for placement on the eye. This process requires touching the lens multiple times, which can transfer contaminants or pathogens from the hand to the lens and ultimately to the eye. Not only is this handling experience unsanitary, but it is also unduly cumbersome, messy, and mechanically stressful to the lens, which can tear, rip, or distort when overly manipulated. While some packages have been designed to present the lens in a convex-side-up orientation to obviate the need for flipping the lens, they often still require the lens to be "fished" from the packaging solution or otherwise necessitate manipulation of the lens and/or multiple touches of the lens to achieve transfer of the lens to the eye.

In view of the growing awareness around ocular health and the customer demand for a more convenient experience, a need has arisen for contact lens packaging that enables a less messy and more sanitary contact lens handling process. In one respect, it would be ideal to provide wearers of contact lenses with a "touchless" or "no touch" package—that is, a package whereby the wearer of contact lenses can take the lens from the lens storage package via a holder which also allows for the user to position the lens correctly on the eye without touching the lens with his or her fingers. In such a design, there would be no need for transfer and manipulation of the lens from one finger to another before placing the lens on the eye. Providing such a touchless package would not only streamline the lens preparation and insertion process; it would also diminish the possibility of dropping the lens or exposing the lens to bacteria on a wearer's other fingers as the lens is being prepared for orientation and insertion onto the eye, and it also reduces the possibility of touching the side of the lens which is intended to contact the eye.

There remains a need for contact lens packages which provide a consistent touchless removal experience and lens-transfer experience.

II. SUMMARY

It has now been found that some or all the foregoing and related objects may be attained in a contact lens package having one or more aspects described herein. For example, a contact lens package of the invention may house a contact lens and packaging solution wherein the contact lens may be held by surface tension to an intermediate plug, by which the user may insert the contact lens into the wearer's eye. The plug may have an adhesive that temporarily holds the plug to the user's fingertip while the contact lens is inserted into the wearer's eye.

In an aspect, the contact lens package may include a container having a reservoir that houses the contact lens and packaging solution. A plug, at least a portion of which is sized to be received in the container, has an interior facing surface and an exterior facing surface. When the plug is received in the container, the contact lens and the packaging solution are held in a portion of the reservoir between the container and the plug. In an aspect, there is a lid fixable to the container to seal the container. In an aspect, the lid may comprise foil. In another aspect, the lid may be substantially rigid. In another aspect, the lid may include an opening tab. In another aspect, the lid seals the container with the plug therein and with the contact lens and the packaging solution in the portion of the container between the container and the plug. The plug may comprise a partial hyperbolic profile, such as a truncated hyperboloid, in which the diameter of the interior facing surface is less than the diameter of the exterior facing surface. In an aspect, the exterior facing surface may be planar. In an aspect, the interior facing surface may be concave. In another aspect, curvature of the interior facing surface substantially matches a profile of the contact lens to be stored in the container. In an aspect, the contact lens is held by surface tension to the interior facing surface in a convex orientation with respect to the interior facing surface. In an aspect, there may be a surface film on the interior facing surface to facilitate surface tension between the convex surface of the contact lens and the interior facing surface of the plug. In an aspect, the plug is configured to hold the contact lens during insertion of the contact lens into a wearer's eye.

In another aspect, there may be an adhesive on the exterior facing surface of the plug. The adhesive may be releasably adherable to human skin, for example, such that that the adhesive attaches temporarily to a human finger. In another aspect, the adhesive may provide adhesion between the lid and the exterior facing surface. In an aspect, the adhesive may be silicone. In an aspect, when the plug is received in the container, the plug fluidically seals the reservoir of the container. The container may be cylindrical in profile. The container and/or the plug may comprise polypropylene.

In a method of applying a contact lens to a wearer's eye, the contact lens may be stored in a package having a container having a reservoir and a plug in the container, the plug having an interior-facing surface and an exterior-facing surface; such that, when the plug is received in the container, the contact lens and the packaging solution is held in a portion of the reservoir between the container and the plug. In the method, a user removes the plug from the container, the contact lens adhering to the interior-facing surface of the plug via surface tension and in an orientation ready for insertion in the wearer's eye; and applies the contact lens to the wearer's eye. In an aspect, the user may remove a lid from the container before removing the plug from the container. In an aspect, removing the plug from the container is performed by pressing a finger against an adhesive on the exterior-facing surface of the plug, thereby causing the adhesive to adhere to the finger. In an aspect, applying the contact lens is performed without the person applying the contact lens touching the contact lens. The user then withdraws the plug from the contact lens while the contact lens remains in the wearer's eye.

In another aspect of the present invention, the contact lens may be packaged in the container by providing packaging solution in a container; providing a contact lens in a convex up orientation in the container; inserting a plug having a concave face over the contact lens such that the concave face of the plug is adjacent to the contact lens. In an aspect, the plug may act as the seal. In another aspect, the packaging may comprise sealing the container by applying a lid to the container.

In another aspect of the present invention, a support for applying a contact lens to a wearer's eye, may comprise a plug having a first end surface and a second end surface, wherein the first surface is concave, and the second surface is substantially planar, the curvature of the concave surface substantially matches a profile of the contact lens.

III. BRIEF DESCRIPTION OF THE DRAWINGS

The foregoing and other features and advantages of the invention will be apparent from the following, more particular description of preferred embodiments of the invention, as illustrated in the accompanying drawings.

IV. DETAILED DESCRIPTION

Figure 1:
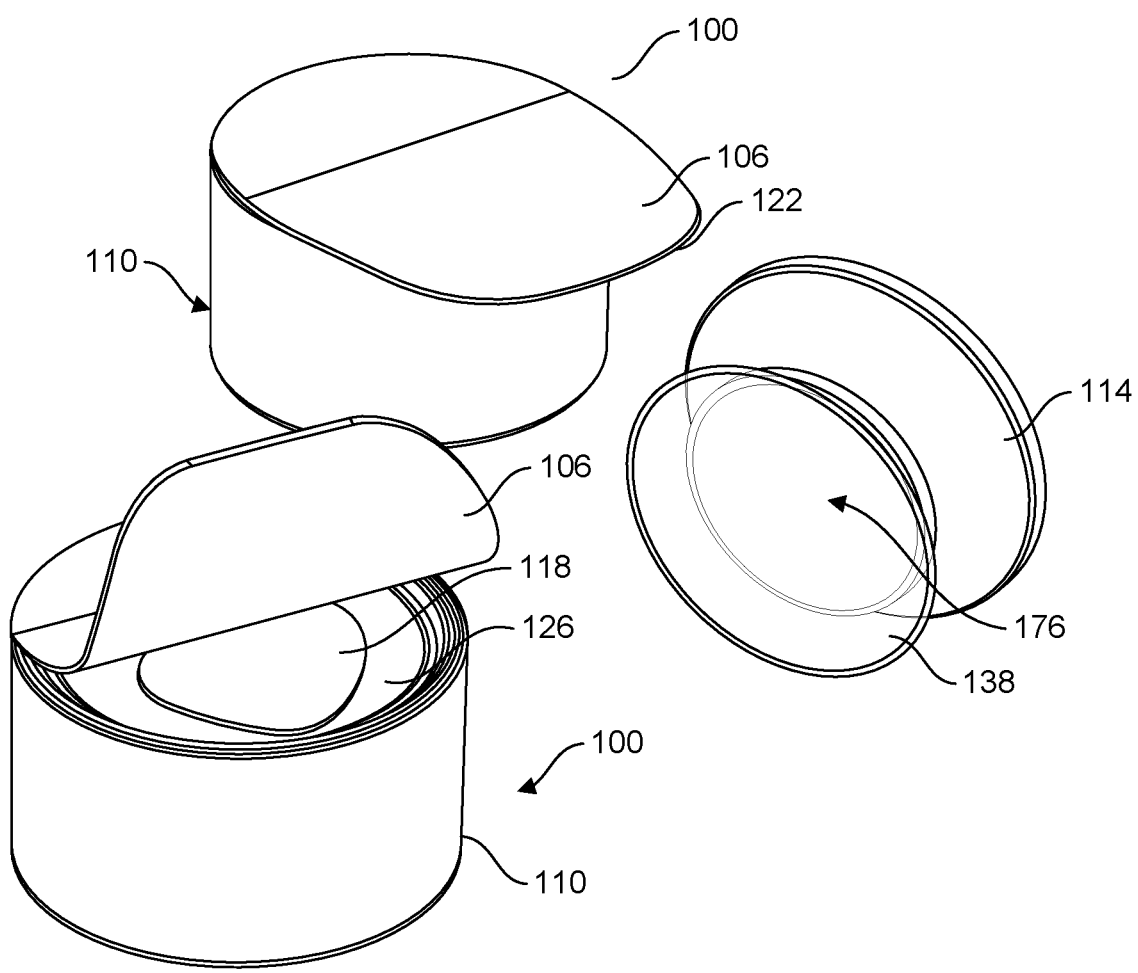
FIG. 1 illustrates a no touch contact lens package according to an exemplary embodiment of the present invention.

Reference will now be made in detail to representative embodiments illustrated in the accompanying drawings wherein reference numerals indicate certain elements. The following descriptions are not intended to limit the myriad embodiments to one preferred embodiment. To the contrary, it is intended to cover alternatives, modifications, and equivalents as can be included within the spirit and scope of the described embodiments as defined by the appended claims.

References to "one embodiment," "an embodiment," "some embodiments," "an example embodiment," etc., indicate that the embodiment described may include a particular feature, structure, aspect, or characteristic, but every embodiment may not necessarily include the particular feature, structure, or characteristic. Moreover, such phrases are not necessarily referring to the same embodiment. Further, when a particular feature, structure, aspect, or characteristic is described in connection with an embodiment, it is submitted that it is within the knowledge of one skilled in the art to effect such feature, structure, or characteristic in connection with other embodiments whether or not explicitly described.

As used herein, the following terms have the following meaning. A benefit of the certain embodiments the present invention is that they facilitate consistent no-touch lens transfer from the package to a wearer's eye without the lens inverting, falling off the holder or further manipulation. The lens also desirably "sits up" on the holder without collapsing or inverting and then transfers to the eye when placed there. Packages of certain embodiments may provide the desired no-touch transfer across a range of wearer finger sizes, and dab pressures. Use of no-touch package with a holder may reduce the effects of environmental conditions, such as the temperature and whether the finger is wet or dry, which may impact lens transfer.

Lens(es) or contact lens(es) refer to ophthalmic devices that reside on the eye. They have a generally hemispheric shape and can provide optical correction, cosmetic enhancement, UV blocking and visible light or glare reduction, therapeutic effect, including wound healing, delivery of drugs or neutraceuticals, diagnostic evaluation or monitoring, or any combination thereof. The term lens includes soft hydrogel contact lenses, which are generally provided to the consumer in a package in the hydrated state, and have a relatively low moduli, which allows them to conform to the cornea. Contact lenses suitable for use with the packages of the present invention include all hydrated contact lenses, including conventional and silicone hydrogel contact lenses.

A hydrogel is a hydrated crosslinked polymeric system that contains water in an equilibrium state, and may contain at least about 25%, or at least 35% water in the hydrated state. Hydrogels typically are oxygen permeable and biocompatible, making them excellent materials for producing contact lenses.

Conventional hydrogel contact lenses do not contain silicone containing components, and generally have higher water content, lower oxygen permeability, moduli, and shape memories than silicone hydrogels. Conventional hydrogels are prepared from monomeric mixtures predominantly containing hydrophilic monomers, such as 2-hydroxyethyl methacrylate ("HEMA"), N-vinyl pyrrolidone ("NVP") or polyvinyl alcohols. U.S. Pat. Nos. 4,495,313, 4,889,664 and 5,039,459 disclose the formation of conventional hydrogels. Conventional hydrogels may be ionic or non-ionic and include polymacon, etafilcon, nelfilcon, ocufilcon lenefilcon and the like. The oxygen permeability of these conventional hydrogel materials is typically below 20-30 barrers.

Silicon hydrogel formulations include balafilcon samfilcon, lotrafilcon A and B, delfilcon, galyfilcon, senofilcon A, B and C, narafilcon, comfilcon, formofilcon, riofilcon, fanfilcon, stenfilcon, somofilcon, kalifilcon and the like. "Silicone hydrogels" refer to polymeric networks made from at least one hydrophilic component and at least one silicone-containing component. Silicone hydrogels may have moduli in the range of 60-200, 60-150 or 80-130 psi, water contents in the range of 20 to 60%. Examples of silicone hydrogels include acquafilcon, asmofilcon, balafilcon, comfilcon, delefilcon, enfilcon, fanfilcon, formofilcon, galyfilcon, lotrafilcon, narafilcon, riofilcon, samfilcon, senofilcon, somofilcon, and stenfilcon, verofilcon, including all of their variants, as well as silicone hydrogels as prepared in U.S. Pat. Nos. 4,659,782, 4,659,783, 5,244,981, 5,314,960, 5,331,067, 5,371,147, 5,998,498, 6,087,415, 5,760,100, 5,776,999, 5,789,461, 5,849,811, 5,965,631, 6,367,929, 6,822,016, 6,867,245, 6,943,203, 7,247,692, 7,249,848, 7,553,880, 7,666,921, 7,786,185, 7,956,131, 8,022,158, 8,273,802, 8,399,538, 8,470,906, 8,450,387, 8,487,058, 8,507,577, 8,637,621, 8,703,891, 8,937,110, 8,937,111, 8,940,812, 9,056,878, 9,057,821, 9,125,808, 9,140,825, 9,156,934, 9,170,349, 9,244,196, 9,244,197, 9,260,544, 9,297,928, 9,297,929 as well as WO 03/22321, WO 2008/061992, and US 2010/0048847. These patents are hereby incorporated by reference in their entireties. Silicone hydrogels may have higher shape memory than conventional contact lenses.

Hydrogel lenses are viscoelastic materials. Contact lenses can form optical distortions if the lens interacts with either the package or any air bubble in the package. The extent of the optical distortions, and the length of time needed for the distortions to relax out will vary depending on the chemistry, and to a lesser extent, geometry of the lens. Conventional lens materials, such as polyhydroxyethyl methacrylate-based lenses like etafilcon A or polymacon have low loss modulus and tan delta compared to silicone hydrogels and may form fewer and less severe optical distortions as a result of contact with packaging. The incorporation of silicones (which generally increase the bulk elastic response), wetting agents such as PVP (which generally increase the viscous response) or coatings of conventional hydrogel materials (which may lower the elastic response at the lens interface) can alter the lens viscoelastic properties. Conventional hydrogel contact lenses and silicone hydrogel contact lenses having short or stiff crosslinking agents and or stiffening agent have short shape memories and may be less susceptible to deformation during storage. As used herein, high or higher shape memory hydrogels display optical distortions from contact with an air bubble or package of at least about 0.18 after 5 weeks of accelerated aging at 55° C. Viscoelastic properties, including loss modulus and tan delta, can be measured using a dynamic mechanical analysis.

The contact lenses can be of any geometry or power, and have a generally hemispherical shape, with a concave posterior side which rests against the eye when in use and a convex anterior side which faces away from the eye and is contacted by the eyelid during blinking.

The center or apex of the lens is the center of the lens optic zone. The optic zone provides optical correction and may have a diameter between about 7 mm and about 10 mm. The lens periphery or lens edge is the edge where the anterior and posterior sides meet.

The wetted lens is the contact lens and any residual packaging solution attached to it after packaging solution drainage. Wetted contact is the aggregated contact area between the wetted lens and a lens support.

Embodiments may include a container providing a sealable cavity also interchangeably referred to as a reservoir. The cavity may have any convenient form and may comprise a package bottom floor and walls, each of which are described in detail below. As used herein, the phrases "the lid", "a lid", "the bottom floor", "a bottom floor", "the container" and "a container" encompass both the singular and plural. The lid and container are sealed to each other to form a cavity which holds the contact lens, plug and packaging solution in a sterile state during shipping and storage prior to use. The contact lens package is made from materials which are compatible with the contact lens and solution, as well as retortable and biologically inert.

"Film" or "multilayer film" are films used to seal the package and are often referred to as lidstock. Multilayer films used in conventional contact lens packages may be used in the packages of the present invention as the base, a component of the lid, or both. Multilayer films comprise a plurality of layers, including barrier layers, including foil layers, or coatings, seal layers, which seal the film to the rest of the package, and may also comprise additional layers selected from peel initiation layers, lamination layers, and layers that improve other package properties like stiffness, temperature resistance, printability, puncture resistance, barrier resistance to water or oxygen and the like. The multilayer films form a steam sterilizable (retortable) seal. The multilayer film can include PET, BON or OPP films layers to increase stiffness and temperature resistance, or to EVOH or PVDC coatings to improve barrier resistance to oxygen or moisture vapor.

An "unopened state" or "unopened" as used herein refers to a contact lens package that is closed and houses a contact lens in solution.

An "opened state" or "opened" as used herein refers to a contact lens package after the sterile seal has been broken. Depending on the context described herein, the open state extends to the state of the package when the user has manipulated the package to cause the lens to be lifted out of the packaging solution for transfer by the user.

A "wearer" or "user" as used herein refers to a person opening a contact lens package. The user is generally referred to as the person who both opens the package and transfers the contact lens contained therein to their eye. However, the user in some contexts may be a person handling the lens package on behalf of the wearer, such an eye care provider ("ECP") or another individual demonstrating for or assisting the wearer.

Packaging solution is any physiologically compatible solution, which is compatible with the selected lens material and packaging. Packaging solutions include buffered solutions having a physiological pH, such as buffered saline solutions. The packaging solution may contain known components, including buffers, pH and tonicity adjusting agents, lubricants, wetting agents, nutraceuticals, pharmaceuticals, in package coating components and the like.

The container may form the bottom of the package. It can be made from any material suitable for packaging medical devices, including plastic. The packaging lid generally resides at the upper portion the package and seals with the container to form a cavity containing at least a portion of the plug, lens, and packaging solution. The lid may be made from any material suitable for packaging medical devices, including a molded sheet of foil or plastic, laminate films, or plastic. Packages comprising plastic for one structure and foil or laminated films as the other, or packages comprising foil or laminated films as the outer layer for the lid and base are known in the art and are examples of suitable combinations.

References throughout this description to injection molding processes and the use of materials conventionally applied to injection molding should be understood as exemplary. Those of skill in the art will appreciate that other means of manufacture are possible within the scope of the appended claims, including but not limited to alternative molding processes, thermoforming, 3D printing, and the like. Likewise, references to heat seals and heat sealing are exemplary to embodiments described herein. Other means of securing packaging components will be apparent to those skilled in the art, including the use of adhesive, glue, thermal bonding, welding such as heat, ultrasonic or laser welding, or a mechanical trap, and the like.

Certain aspects of the invention may serve to reduce or prevent significant optical damage to the contact lens due to interactions with air bubbles or the interior of the lens package that may arise during storage or transit due to gravitational or other forces, such as mechanical pressure being applied from outside of the package. As used herein, significant optical damage means a root-mean-squared (RMS) value equal or greater than about 0.08 μm.

FIG. 1 illustrates a contact lens no touch package in an unopened state and a state in which a film used as a lid to seal the package is partially opened. As shown, an embodiment of the contact lens package 100 includes a lid 106 and a container 110. The contact lens package 100 further includes a removable plug 114 within a cavity/reservoir (not shown) of the container 110. In the illustrated embodiment, there is a tacky or adhesive substance 118, such as low tack silicone, between an exterior-facing surface 126 of the removable plug 114 and the lid 106. The plug 114 also has an interior-facing surface 130, which faces the contact lens 138 in the assembled contact lens package 100. The plug 114 also serves a holder, by which the user moves the contact lens 138 and inserts the contact lens 138 into the eye of a wearer. In an alternative embodiment, the exterior facing surface of the plug may be configured to be grasped by a user, perhaps by a thumb and forefinger and held by the user during insertion of the contact lens.

Figure 2:
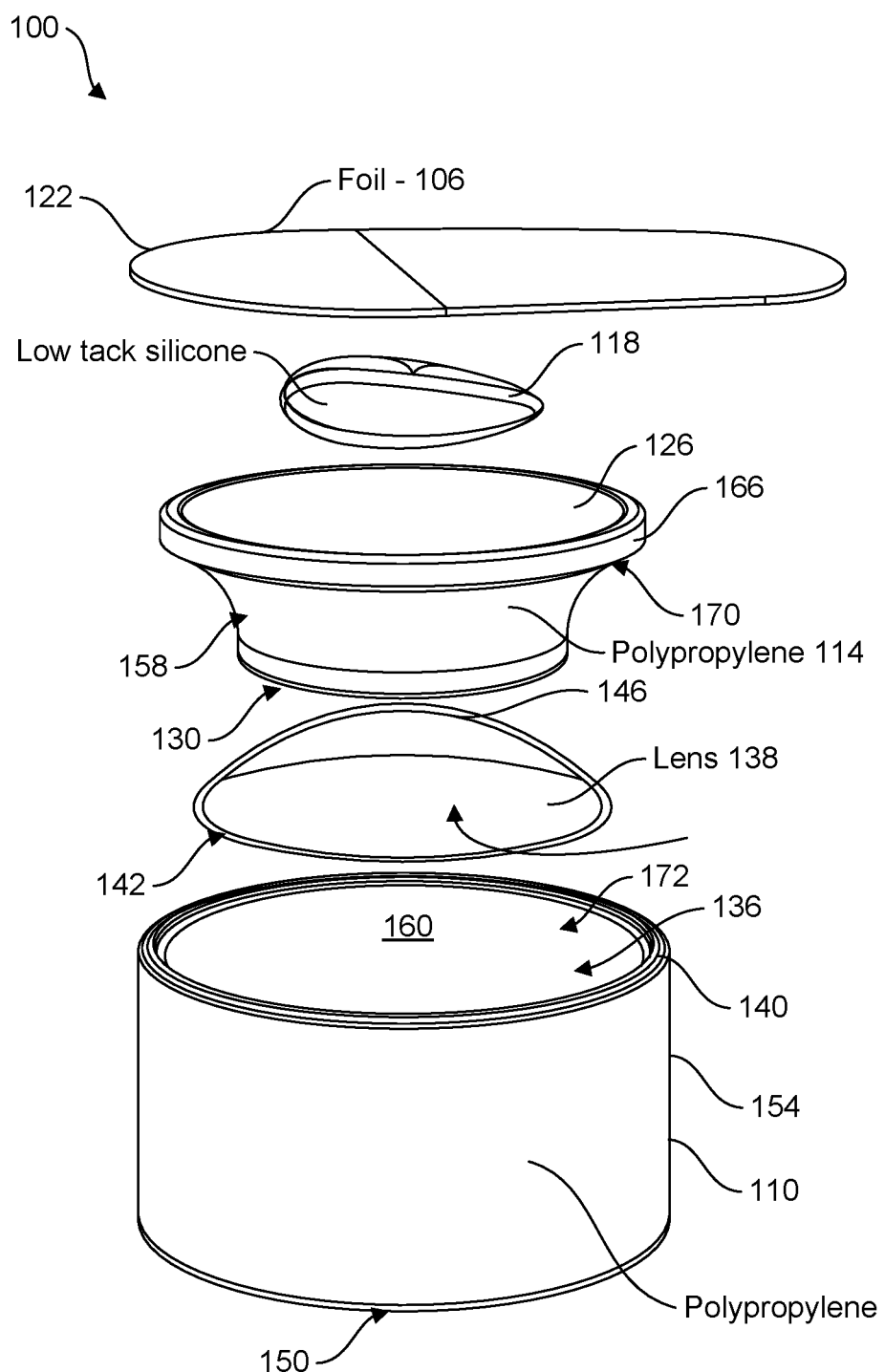
FIG. 2 is an exploded view of the components of a no touch contact lens package according to an exemplary embodiment of the present invention.

FIG. 2 is an exploded view of the components of the contact lens package 100 with a contact lens 138 illustrating the packaging of the contact lens 138 in an embodiment of the contact lens package according to principles described herein.

As can be seen in FIG. 2, the container 110 includes a cavity/reservoir 136. While shown in the figures as being cylindrical, the shape of the container 110 and reservoir 136 are not so limited and may be of any shape or cross-section appropriate for providing the requirements of a contact lens package, such as sterile and liquid-tight. The container has a bottom floor 150 and side wall(s) 154 such that the container cavity/reservoir 136 is provided therein. The cavity/reservoir 136 is liquid tight such that contact lens packaging solution held therein is held within the cavity/136. Opposite the bottom floor 150 of the container 110 is an opening 158. There may be a rim (not shown) along an inner periphery of the wall 154.

The rim (not shown) may be at an end of the container comprising the opening. The rim (not shown) may be immediately adjacent the opening or may be positioned along an interior of the wall 154. The rim (not shown) may abut or engage an outer periphery of a portion of the plug 114 to reduce or prevent motion of the plug 114 toward the floor of the cavity/reservoir when the plug 114 is inserted into the cavity/reservoir 136. The container 110 may further include an upper edge, rim, or surface 140 at the end of the container having the opening for attaching the lid 106 thereto, as described later herein. In an aspect, diameter of the reservoir is matched to the contact lens, such that the contact lens fits in the reservoir in a "bowl-down" (convex with respect to the plug) configuration, with the periphery 142 of the contact lens closely adjacent or touching an interior wall of the cylinder making up the reservoir 136. In the "bowl-down" orientation, a peripheral edge 142 of the contact lens 138 may rest on a floor (not shown) of the cavity/reservoir 136. In a packaged state, the cavity/reservoir further includes packaging solution for maintaining a contact lens 138 in an appropriate environment. The container 110 may comprise a polymer, such as polypropylene, or any other suitable material. Injection molding or other known methods may be used to make the container, and it may comprise a unitary or multi-piece structure, so long as it is capable of holding liquid without leaking.

The plug 114 is sized to be received in the cavity/reservoir 136. For example, in the illustrated embodiment, the reservoir 136 is a cylindrical cavity, and the plug 114 has a circular cross-section matched to the opening of the reservoir 136. Depth of the cavity/reservoir 136 is sized such that the plug 114 and a contact lens 138 may be received in the reservoir 136 without significantly impinging or damaging the contact lens 138 within the cavity 136. The plug 114 includes an exterior facing surface 126 and an interior facing surface 130, such that the interior facing surface faces the floor (not shown) of the reservoir in the assembled contact lens package. The plug may comprise a partial hyperboloid profile, e.g. an upper half of a hyperboloid. For example, the exterior facing surface (e.g., the top) of the plug 114 may be larger than the interior facing surface 130. While described herein as hyperbolic, the shape of the plug is not so limited and may be of any shape sufficient for the purposes described herein. For example, the plug may be substantially or generally cylindrical, conical, rectangular, trapezoidal, even partially spherical, etc.

As illustrated in FIGS. 1 and 2, the exterior facing surface 126 is substantially planar, but may include a depression of concave surface, e.g. suitable for a finger. As shown in FIG. 1 in an assembled configuration, the exterior-facing surface 126 may not be coextensive with the upper edge of the container 110, such that the exterior-facing surface is within the cavity, e.g., below the container opening 160. The plug 114 may have a wall or walls 158 of any suitable profile extending between the exterior facing surface 126 and the interior facing surface 130. The plug may further include an engagement rim 166 for abutting an interior surface 172 of the container 110 of the cavity/reservoir 136. The plug wall 158 or the engagement rim 166 may provide an interference fit with the interior surface 172 of the container. The engagement rim have an underside 170 that abuts the rim (not shown) to reduce or prevent motion of the plug 114 toward the bottom of the cavity/reservoir 136.

The plug interior facing surface 130 is shaped to abut or be adjacent to the convex surface of the contact lens. For example, the plug interior facing surface 130 is concave, with a curvature similar to or matched with a curvature of the convex surface of the contact lens 138 (when the contact lens is in the position for insertion (i.e., not improperly inverted).

The plug 114 may be hollow or solid, or may include interior support structures. The plug 114 may comprise a polymer, such as polypropylene, or any other suitable material. Injection molding or other known methods may be used to make the plug, and it may comprise a unitary or multi-piece structure.

In the illustrated embodiment of FIGS. 1 and 2, as stored, an apex 146 of the contact lens 138 is adjacent the interior facing surface 130 of the plug 114. The contact lens is held to the interior facing surface 130 by surface tension. The interior facing surface 130 of the plug 114 may include a surface film layer 176 to cause surface tension between the convex surface of the contact lens 138 and the interior facing surface 130 of the plug 114. The surface tension should be sufficient to cause the contact lens 138 to move with the movement of the plug upon removal from the cavity/reservoir. In an aspect, sufficient surface tension may be provided without the surface film layer depending on the properties of the convex surface of contact lens 138, the properties of the interior facing surface 130 of the plug 114, and the properties of packaging solution.

When the plug 114 is received within the cavity/reservoir, the container reservoir is fluidically sealed, and the contact lens and the packaging solution is held in a portion of the reservoir between the container bottom floor 150 and the plug 114.

In an aspect, there is a tacky or adhesive substance 118, such as low tack silicone, on the exterior-facing surface 126 of the removable plug 114. The adhesive 118 is releasably adherable to human skin, for example, such that it can be touched by a user, causing the plug 114 to be held to the finger and, therefore, a contact lens held to the plug by surface tension to be controlled by the user's finger without actually contacting the user's finger. As noted above, the exterior facing surface 126 may be slightly offset or may even be concave for hosting the adhesive. The adhesive 118 may also serve the purpose of holding the lid 106 in position until removal.

As can be seen in FIGS. 1 and 2, the lid 106 may be a multilayer film or laminated foil seal that is heat sealed to an upper portion of the package.

The lid 106 may include an overhang, which provides an opening tab 122, by which the user may grasp and remove the lid 106 from the container. For example, a portion of the foil that makes up the lid 106 may extend laterally beyond the wall 154 of the container 150. The color of the overhang/tab 122 may be opaque or semi- or fully translucent, as desired. In this way, the colored handle serves as a visual indication to the wearer of the correct package orientation for opening and that the package is to be opened by engaging the opening tab 122. Although not shown herein, there may be a grasping member extending from the container under the opening tab to assist in grasping the opening tab. The grasping member may be frangible from the container and adhered to the opening tab or may be unitary with the container such that the grasping member is held and the overhang opening tab 122 pulled away from the grasping member while a user holds the grasping member.

The container may include a contact lens support upon which the bowl of the contact lens rests, but such is not necessary. In other words, with or without a contact lens support within the reservoir 136, a peripheral edge 142 of the contact lens 138 may rest on a floor (not shown) of the reservoir. The lens support may keep the lens in the desired convex orientation (bowl down relative to the plug) and position (centered under the plug) during shipping and storage. The lens support may provide a structure under the lens to allow, upon removing the plug and lens from the reservoir, the packaging solution to drain from the lens.

The plug has a sufficient number of contact points with the lens to prevent the lens from collapsing onto, rotating off or translating across the plug. This allows the apex of the lens to be supported by the lens's own elastic stiffness, or to minimize sinking of the lens apex while limiting the contact area between the plug and lens.

For lenses made from polymers with longer shape memory, the lens support may be designed to limit contact between the lens and plug during storage. Such contact may be distributed around the lens peripheral edge.

Figure 3B:
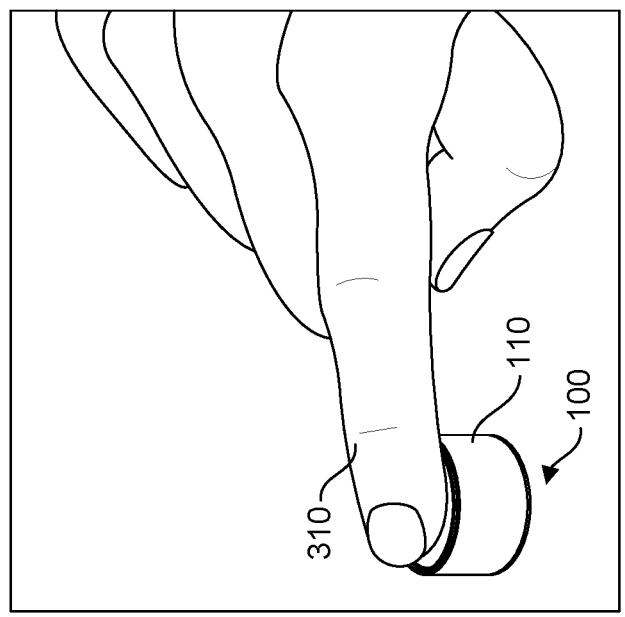
FIGS. 3A-3D illustrate steps of handling a contact lens package containing a contact lens in packaging solution according to an exemplary embodiment of the present invention.
Figure 3A:
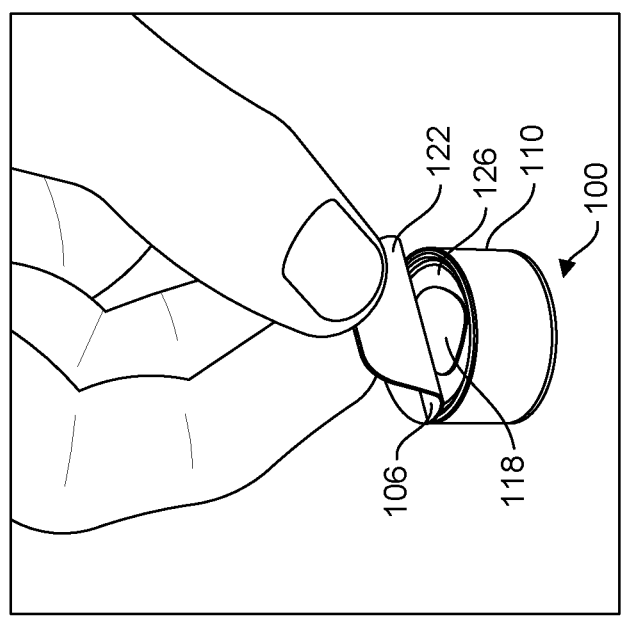

With reference to the figures, FIGS. 3A-3D illustrate steps of handling a contact lens package containing a contact lens in packaging solution according to an exemplary embodiment of the present invention. An unopened contact lens package 100 having a container 110, an opening tab 122, and a lid 106, is shown at FIG. 3A. FIG. 3A also shows the exterior facing surface 126 of the plug and adhesive 118. In the illustrated embodiment, the opening tab 122 is part of the lid 106. In a first step shown in FIG. 3A, a wearer/user holds an unopened contact lens package 100 and pulls the opening tab 122 of the lid 106 of the package 100. As illustrated at in FIG. 3A, pulling the opening tab 110 away from the top of the container causes the lid 106 to be removed from the top of the container 110, exposing adhesive 118 on the exterior facing surface 126 of the plug. Although not required, the wearer may grasp the package 100 with one hand and pull the opening tab 122 with the other hand to remove the lid 106 from the container 106, exposing the adhesive 118.

Figure 3D:
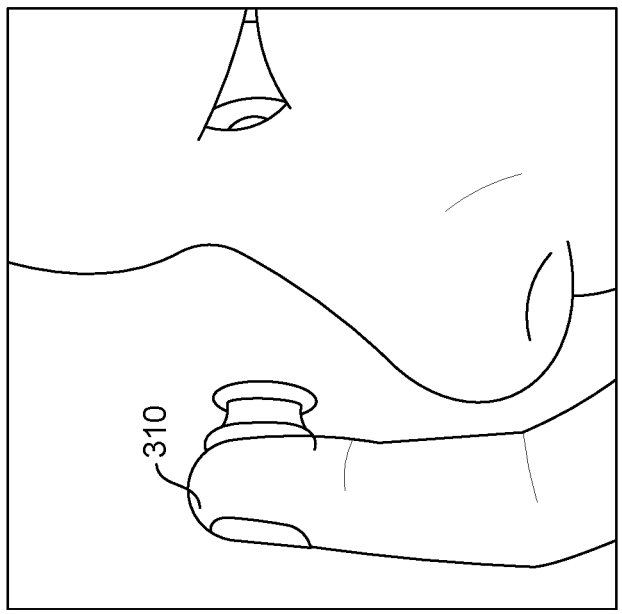
Figure 3C:
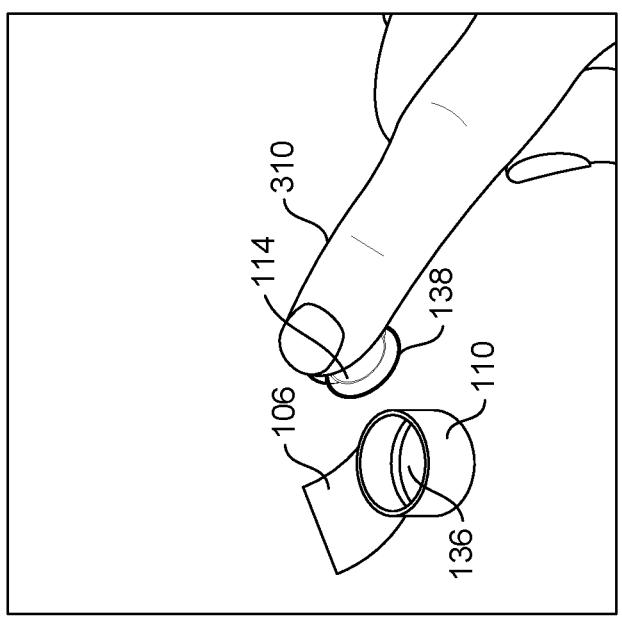

As illustrated in FIG. 3B, a user places the tip of a finger 310 onto the adhesive on the exterior facing surface of the plug, which temporarily/removably adheres to the skin of the fingertip with sufficient force to allow for the user to pull the plug from the container 110 via the adhesive to fully remove the plug 114 and the contact lens 138 from the cavity/reservoir of the container. As shown in FIG. 3C, the plug 114 is held to the fingertip by the adhesive 118 and the contact lens 138 is held to the interior facing surface of the plug 114 via surface tension, as described above.

Because the contact lens 138 is stored in the reservoir in a bowl-down configuration, it is oriented for insertion into the wearer's eye. As shown in FIG. 3D, the user moves his/her fingertip with the plug 114 and contact lens attached thereto into the proper position for moving the contact lens toward the wearer's eye for insertion according to known steps, except that the plug allows the fingertip to not touch the contact lens, thereby substantially preventing or reducing contamination of the lens that might be caused by touching non-sterile surfaces before insertion, by mimicking the motions of application with a finger.

Although not shown in the figures, after the contact lens is inserted in the wearer's eye, force, such as surface tension, holding the contact lens in the wearer's eye allows the user to withdraw the plug from the contact lens convex surface. The user may then remove the plug and adhesive from his/her finger and dispose of the plug and the container. Throughout the disclosed process, the container holds the packaging solution, allowing the solution to be available to the user/wearer for rewetting or rinsing the contact lens during the insertion process.

Packaging of the contact lens may be performed by providing packaging solution in a container. A single contact lens, in a convex up position, may be then placed in the container. A plug, as described above, may then be provided in the container above the contact lens. The plug may have an adhesive on its exterior facing surface before insertion into the container or the adhesive may be added after the plug has been placed into the container. A lid is then provided over the plug and the opening of the container. The lid may be a multilayer film or laminated foil seal that is heat sealed to an upper portion of the container over the plug and opening.

In another aspect of the present invention, a support for applying a contact lens to a wearer's eye, may comprise a plug having a first end surface and a second end surface, wherein the first surface is concave, and the second surface may be substantially planar or depressed/concave. The plug may comprise a polymer material such as polypropylene. The curvature of the concave surface of the first end surface substantially matches a profile of the contact lens.

In any of the above-described embodiments, it is anticipated the wearer is the user, but the above-described embodiments also describe the situation in which the wearer is not the same person as the user, for example, in a medical or caretaker setting in which a caregiver applies a contact lens to the eye of a patient.

The foregoing description, for purposes of explanation, used specific nomenclature to provide a thorough understanding of the described embodiments. However, it will be apparent to one skilled in the art that many of the specific details are not required in order to practice the described embodiments. Thus, the foregoing descriptions of the specific embodiments described herein are presented for the purposes of illustration and description. They are not targeted to be exhaustive or to limit the embodiments to the precise forms disclosed. It will be apparent to one of ordinary skill in the art that many modifications and variations are possible in view of the above teachings.

The Summary and Abstract sections may set forth one or more but not all exemplary embodiments of the present invention as contemplated by the inventors, and thus, are not intended to limit the present invention and the appended claims in any way.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The packages of the present invention may be manufactured using known materials and processes. The packaging materials may be virgin, recycled or a combination thereof. The volume within the package cavity can vary depending on the design selected.

Not all the features described herein need to be incorporated into every package, and those of skill in the art, using the teachings herein, can combine the features to provide a wide variety of improved contact lens packages. In summary, the contact lens packages of the present invention incorporate several novel functionalities which may be combined in a wide variety of combinations as described herein to provide the desired improved and/or touchless packaging. The breadth and scope of the present invention should not be limited by any of the above-described exemplary embodiments but should be defined only in accordance with the following claims and their equivalents.

What is claimed is:

1. A contact lens package, comprising:
   a container having a reservoir that houses a contact lens and packaging solution; and
   a plug, a portion of the plug sized to be received in the container, the plug having an interior-facing surface and an exterior-facing surface;
   such that, when the plug is received in the container, the contact lens and the packaging solution are held in a portion of the reservoir between the container and the plug; and
   further comprising a surface film layer on the interior-facing surface to cause surface tension between the contact lens and the interior-facing surface.

2. The contact lens package of claim 1, further comprising a lid fixable to the container to seal the container.

3. The contact lens package of claim 2 wherein the lid comprises foil.

4. The contact lens package of claim 2, wherein the lid is substantially rigid.

5. The contact lens package of claim 2, wherein the lid further comprises an opening tab.

6. The contact lens package of claim 2, wherein the lid seals the container with the plug therein and with the contact lens and the packaging solution in the portion of the reservoir between the container and the plug.

7. The contact lens package of claim 1, wherein the plug comprises a partial hyperboloid profile.

8. The contact lens package of claim 7, wherein the partial hyperboloid profile is truncated, such that a diameter of the interior-facing surface is less than the diameter of the exterior-facing surface.

9. The contact lens package of claim 2, further comprising an adhesive on the exterior-facing surface between the exterior-facing surface and the lid.

10. The contact lens package of claim 9, wherein the adhesive is releasably adherable to human skin.

11. The contact lens package of claim 9, wherein the adhesive is releasably adherable to human skin such that the adhesive attaches temporarily to a human finger.

12. The contact lens package of claim 9, wherein the adhesive provides adhesion between the lid and the exterior-facing surface.

13. The contact lens package of claim 1, wherein the exterior-facing surface is planar.

14. The contact lens package of claim 1, wherein the interior-facing surface is concave.

15. The contact lens package of claim 1, wherein a curvature of the interior-facing surface substantially matches a profile of the contact lens.

16. The contact lens package of claim 1, wherein the reservoir houses the contact lens in convex position relative to interior-facing surface.

17. The contact lens package of claim 1, further comprising an adhesive on the exterior-facing surface.

18. The contact lens package of claim 17, wherein the adhesive is releasably adherable to human skin.

19. The contact lens package of claim 17, wherein the adhesive is releasably adherable to human skin such that the adhesive attaches temporarily to a human finger.

20. The contact lens package of claim 17, wherein the adhesive is silicone.

21. The contact lens package of claim 1, wherein the plug received in the container fluidically seals the reservoir of the container.

22. The contact lens package of claim 1, wherein the container is cylindrical.

23. The contact lens package of claim 1, wherein the container comprises polypropylene.

24. The contact lens package of claim 1, wherein the plug comprises polypropylene.

25. The contact lens package of claim 1, wherein the plug is configured to hold the contact lens during insertion of the contact lens to a wearer's eye.

26. The contact lens package of claim 25, wherein the contact lens is held by the interior-facing surface of the plug.

27. The contact lens package of claim 25, wherein the plug is configured to be held by a person during insertion of the contact lens to the wearer's eye.

28. The contact lens package of claim 27, wherein the plug is configured to be held by the person by adherence of an adhesive on the exterior-facing surface of the plug to the person's finger.

29. A method of applying a contact lens to a wearer's eye, the contact lens stored in a package comprising a container having a reservoir and a plug in the container, the plug having an interior-facing surface and an exterior-facing surface; such that, when the plug is received in the container, the contact lens and the packaging solution is held in a portion of the reservoir between the container and the plug, the method comprising:
   removing the plug from the container, the contact lens adhering to the interior-facing surface of the plug via surface tension and in an orientation ready for insertion in the wearer's eye; and
   applying the contact lens to the wearer's eye;
   wherein the plug further comprises a surface film layer on the interior-facing surface to cause surface tension between the contact lens and the interior-facing surface.

30. The method of claim 29, wherein the removing the plug from the container is performed by pressing a finger against an adhesive on the exterior-facing surface of the plug, thereby causing the adhesive to adhere to the finger.

31. The method of claim 29, wherein the applying the contact lens is performed without a person applying the contact lens touching the contact lens.

32. The method of claim 29, further comprising withdrawing the plug from the contact lens after applying the contact lens to the wearer's eye.

33. The method of claim 29, the contact lens packaging further comprising a lid sealing the plug, contact lens and packaging solution in the container, the method further comprising, removing the lid prior to removing the plug from the container.

34. A method of packaging a contact lens, comprising:
   providing packaging solution in a container;
   providing a contact lens in a convex up orientation in the container; and
   inserting a plug having a concave face over the contact lens such that the concave face of the plug is adjacent to the contact lens;
   wherein the plug comprises an interior-facing surface and an exterior-facing surface, and a surface film layer on the interior-facing surface to cause surface tension between the contact lens and the interior-facing surface.

35. The method of claim 34, further comprising sealing the container by applying a lid to the container.

* * * * *